United States Patent
Crozet et al.

(10) Patent No.: US 12,076,429 B2
(45) Date of Patent: *Sep. 3, 2024

(54) ESTOLIDE COMPOSITION FOR TOPICAL APPLICATIONS

(71) Applicant: TOTALENERGIES ONETECH, Courbevoie (FR)

(72) Inventors: Delphine Crozet, Villeurbanne (FR); Alice Limoges, Ternay (FR); Benjamin Swoboda, Orgeval (FR)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/909,038

(22) PCT Filed: Mar. 17, 2021

(86) PCT No.: PCT/FR2021/050440
§ 371 (c)(1),
(2) Date: Sep. 2, 2022

(87) PCT Pub. No.: WO2021/186131
PCT Pub. Date: Sep. 23, 2021

(65) Prior Publication Data
US 2023/0107326 A1    Apr. 6, 2023

(30) Foreign Application Priority Data
Mar. 19, 2020  (FR) .................................... 2002719

(51) Int. Cl.
| | | |
|---|---|---|
| *A61K 8/37* | (2006.01) |
| *A61K 8/34* | (2006.01) |
| *A61K 8/36* | (2006.01) |
| *A61Q 1/00* | (2006.01) |
| *C07C 69/675* | (2006.01) |

(52) U.S. Cl.
CPC .................. *A61K 8/37* (2013.01); *A61K 8/34* (2013.01); *A61K 8/361* (2013.01); *A61Q 1/00* (2013.01); *C07C 69/675* (2013.01); *A61K 2800/10* (2013.01)

(58) Field of Classification Search
CPC ......... C07C 69/67; C07C 69/675; C11C 3/00; C11C 1/10; C11C 3/003; A61K 8/37; A61K 8/375; A61K 8/361; A61K 8/34; A61K 2800/10; A61Q 1/00; A61Q 19/00
See application file for complete search history.

(56) References Cited

U.S. PATENT DOCUMENTS

| | | |
|---|---|---|
| 2009/0181060 A1 | 7/2009 | Crotogino |
| 2009/0214453 A1 | 8/2009 | Mueller et al. |
| 2013/0065970 A1 | 3/2013 | Bredsguard et al. |
| 2013/0324754 A1* | 12/2013 | Bredsguard ............ C11C 3/003 554/122 |

FOREIGN PATENT DOCUMENTS

| | | |
|---|---|---|
| EP | 1247519 | 10/2002 |
| FR | 2964865 | 3/2012 |
| JP | 2008174514 | 7/2008 |

OTHER PUBLICATIONS

International Journal of Toxicology, (19910000), vol. 10, No. 1, pp. 9-19.

* cited by examiner

*Primary Examiner* — Vishal V Vasisth
(74) *Attorney, Agent, or Firm* — DUANE MORRIS LLP; Gregory M. Lefkowitz; Brandon A. Chan

(57) ABSTRACT

The invention relates to an estolide ester composition with improved sensory properties for cosmetic or pharmaceutical topical applications.

18 Claims, No Drawings

ESTOLIDE COMPOSITION FOR TOPICAL APPLICATIONS

CROSS-REFERENCE TO RELATED APPLICATIONS

This application is a § 371 national stage entry of International Application No. PCT/FR2021/050440, filed on Mar. 17, 2021, which claims priority to French Patent Application No. 2002719, filed on Mar. 19, 2020, the entire contents of which are incorporated herein by reference.

TECHNICAL FIELD OF THE INVENTION

The invention relates to an estolide ester composition for cosmetic, dermatological or pharmaceutical applications, obtained from raw materials of natural origin.

The invention further relates to the use of an estolide ester composition as an emollient in a cosmetic or pharmaceutical composition, in order to improve the sensory properties of said cosmetic or pharmaceutical composition, for topical application in particular on skin, lips, nails, hair or scalp.

STATE OF THE ART

The markets of cosmetics, dermatology and pharmacy are increasingly demanding in terms of ingredients of biological origin for the formulation of their products. Whereas bio-based active ingredients, emulsifiers and vegetable oils have been strongly developed in recent years and are now widely available on the market, emollients of 100% organic origin are still rare.

The emollients currently used in cosmetics are isoparaffins derived from petrochemistry (mainly isododecane and isohexadecane), white oils, silicone oils or ester-based oils (either synthetic or natural), such as vegetable oils. Isoparaffins, white oils and silicone oils are widely distributed because they are very stable and odorless, but they are not derived from a renewable resource. Although volatile silicones such as cyclomethicone have long been considered as emollients and solvents which are harmless on the skin (International Journal of Toxicology, Vol. 10, no. 1, pp. 9-19, 1991), concerns have been expressed in recent years regarding potential harmful effects thereof on the environment and even on human health (in particular octamethylcyclotetrasiloxane).

Ester-based oils have recently been developed.

Document WO 2013/009471 describes estolide compositions for cosmetic applications, the estolides being obtained from unsaturated fatty acids and from saturated fatty acids.

The aim of the present invention is to provide a topical composition with improved physical-chemical and sensory properties.

A further subject matter of the present invention is to provide a stable topical composition with properties suitable for the use thereof.

A further aim of the present invention is to provide a composition which would be obtained from raw materials of biological (non-petrochemical) origin, in particular of a 100% biological origin.

SUMMARY OF THE INVENTION

An estolide ester composition obtained by the process comprising:
a) an addition reaction of a saturated fatty acid composition (C1) to an unsaturated fatty acid composition (C2) in the presence of a catalyst in order to obtain an estolide acid composition (C3), and
b) optionally, a treatment step for removing unsaturated fatty acids and/or saturated fatty acids from the estolide acid composition (C3) and/or a separation step for separating the monoestolides acid from the polyestolides acid present in the estolide acid composition (C3), in order to obtain a treated acid estolide composition (C3bis), and
c) an esterification reaction of the acid estolides of the acid estolide composition (C3), or, if any, of the treated estolide acid composition (C3bis), using an alcohol composition (C4) comprising one or a plurality of linear or branched alcohols with 2 to 6 carbon atoms, in order to obtain an estolide ester composition (C5), said saturated fatty acid composition (C1) comprising saturated fatty monoacids with 10 to 20 carbon atoms, said unsaturated fatty acid composition (C2) comprising at least 85% by weight of mono-unsaturated fatty monoacids with 8 to 22 carbon atoms, with respect to the total weight of the unsaturated fatty acid composition (C2).

According to one embodiment, the estolide ester composition according to the invention is characterized in that the estolide acid composition (C3) undergoes a treatment step for removing the unsaturated fatty acids and/or the saturated fatty acids, preferentially by molecular distillation, in order to obtain a treated estolide acid composition (C3bis).

According to one embodiment, the estolide ester composition according to the invention is characterized in that the estolide acid composition (C3) or, if any (C3bis), undergoes a separation step for separating the monoestolides acid from the polyestolides acid present in the estolide acid composition. According to one embodiment, the estolide ester composition according to the invention is characterized in that, at the end of the esterification reaction, the estolide ester composition (C5) undergoes a treatment step for removing the alcohols, preferentially by molecular distillation.

According to one embodiment, the estolide ester composition according to the invention is characterized in that same comprises at least compounds with the formula (I):

[Chem. 1]

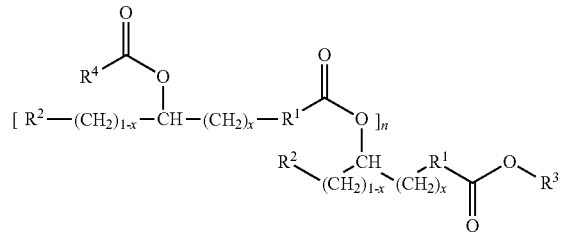

wherein:
R1 is an either linear or branched alkylene radical with from 1 to 17 carbon atoms,
R2 is a hydrogen atom or an either linear or branched alkyl radical with 1 to 17 carbon atoms,
R3 is an either linear or branched alkyl radical with 2 to 6 carbon atoms,
R4 is an either linear or branched alkyl radical with 9 to 19 carbon atoms, x is an integer equal to 0 or 1,
where it is understood that the sum of the carbon atoms of the radicals R1 and R2 ranges from 5 to 17,
n is an integer greater than or equal to zero.

According to one embodiment, the estolide ester composition according to the invention is characterized in that same contains at least 30% by weight, preferentially at least 40% by weight, more preferentially at least 45% by weight of compounds with the formula (I), with respect to the total weight of the estolide ester composition.

According to one embodiment, the estolide ester composition according to the invention is characterized in that same has an iodine value of less than or equal to 12 g/100 g of iodine, preferentially less than or equal to 10 g/100 g of iodine, more preferentially ranging from 1 to 10 g/100 g of iodine, as measured according to the NF EN ISO 3961 method.

The invention further relates to the use of the estolide ester composition according to the invention, in a cosmetic composition, preferentially as an emollient of a cosmetic composition.

The invention further relates to a cosmetic composition comprising:
  at least one estolide ester composition according to the invention, and
  at least one fatty substance and/or at least one cosmetic additive, said fatty substance and said cosmetic additive being different from the estolide esters according to the invention.

According to one embodiment, the cosmetic composition according to the invention comprises, with respect to the total weight of the cosmetic composition:
  from 1 to 80% by weight, preferentially from 5 to 50% by weight, of estolide ester composition(s),
  from 1 to 80% by weight, preferentially from 20 to 60% by weight, of fatty substance(s) different from the estolides chosen from hydrocarbon oils, vegetable oils, vegetable butters, fatty ethers and alcohols, oily alkanes and silicone esters, oils,
  from 0.1 to 30% by weight, preferentially from 1 to 20% by weight, of cosmetic additives chosen from surfactants, preservatives, sequestering agents, antioxidants, perfumes, coloring materials, fillers, thickeners, slimming agents, and mixtures thereof The invention makes it possible to obtain compositions of 100% biological (non-petrochemical) origin with improved sensory properties, suitable for topical applications, in particular for cosmetic, dermatological or pharmaceutical applications.

DETAILED DESCRIPTION OF THE INVENTION

The invention relates to an estolide composition in the form of esters obtained by the process comprising:
  a) an addition reaction of a saturated fatty acid composition (C1) to an unsaturated fatty acid composition (C2) in the presence of a catalyst in order to obtain an acid estolide composition (C3), and
  b) optionally, a treatment step for removing unsaturated fatty acids and/or saturated fatty acids from the acid estolide composition (C3) and/or a separation step for separating the acid monoestolides from the acid polyestolides present in the acid estolide composition (C3) in order to obtain a treated acid estolide composition (C3bis), and
  c) an esterification reaction of the acid estolides of the acid estolide composition (C3), or, if any, of the treated acid estolide composition (C3bis), using an alcohol composition (C4) comprising one or a plurality of either linear or branched alcohols with 2 to 6 carbon atoms, in order to obtain an estolide ester composition (C5),
said saturated fatty acid composition (C1) comprising saturated fatty monoacids with 10 to 20 carbon atoms,
said unsaturated fatty acid composition (C2) comprising at least 85% by weight of mono-unsaturated fatty acids with 8 to 22 carbon atoms, with respect to the total weight of the unsaturated fatty acid composition (C2).

Preferentially, the process of preparing the estolides does not comprise reactions which are different from the addition reactions described in step a) and different from the esterification reactions described in step c).

Preferentially, the estolide ester composition according to the invention is obtained by the process consisting of:
  a) an addition reaction of a saturated fatty acid composition (C1) to an unsaturated fatty acid composition (C2) in the presence of a catalyst in order to obtain an acid estolide composition (C3), and
  b) optionally, a treatment step for removing unsaturated fatty acids and/or saturated fatty acids from the acid estolide composition (C3) and/or a separation step for separating the acid monoestolides from the acid polyestolides present in the acid estolide composition (C3) in order to obtain a treated acid estolide composition (C3bis), and
  c) an esterification reaction of the acid estolides of the acid estolide composition (C3), or, if any, of the treated acid estolide composition (C3bis), using an alcohol composition (C4) comprising one or a plurality of either linear or branched alcohols with 2 to 6 carbon atoms, in order to obtain an estolide ester composition (C5),
said saturated fatty acid composition (C1) comprising saturated fatty monoacids with 10 to 20 carbon atoms,
said unsaturated fatty acid composition (C2) comprising at least 85% by weight of mono-unsaturated fatty acids with 8 to 22 carbon atoms, with respect to the total weight of the unsaturated fatty acid composition (C2).

As defined in the present invention, an "estolide" refers to the product resulting from the reaction of addition of a carboxylic acid function to a carbon-carbon double bond of an unsaturated compound such as an acid or an ester. The term "estolide" in the present invention will refer both to a "monoestolide" and to a "polyestolide".

As defined in the present invention, a "monoestolide" refers to an estolide resulting from a single reaction of addition of an acid function of a saturated fatty acid to an olefinic function of an unsaturated acid or ester. The monoestolide may be in acid form or in ester form depending on the acid or ester form of the unsaturated compound. The monoestolide in acid form can then be esterified in order to obtain a monoestolide ester falling within the scope of the present invention.

As defined in the present invention, a "polyestolide" refers to the product resulting from the reaction between at least two unsaturated compounds (in acid or ester form) followed, optionally, by the reaction with a saturated acid. The polyestolide may be in acid form or in ester form depending on the acid or ester form of the unsaturated compound. The polyestolide in acid form can then be esterified in order to obtain a polyestolide ester falling within the scope of the present invention.

As a preliminary matter, it should be noted that, in the description and the following claims, the expression "comprised between" must be understood as including the limits cited.

Saturated Fatty Acid Composition (C1)

The estolide composition according to the invention can be obtained from a saturated fatty acid composition (C1) comprising at least one either linear or branched fatty acid with 10 to 20 carbon atoms.

Preferentially, the saturated fatty acid composition (C1) comprises at least one saturated fatty acid with 10 to 16 carbon atoms, preferentially from 11 to 14 carbon atoms.

Preferentially, the saturated fatty acid composition (C1) comprises at least one either linear or branched saturated fatty monoacid with 10 to 20 carbon atoms, preferentially from 10 to 16 carbon atoms, preferentially from 11 to 14 carbon atoms.

Preferentially, the saturated fatty acid composition (C1) comprises at least one linear saturated fatty monoacid with 10 to 20 carbon atoms, preferentially from 10 to 16 carbon atoms, preferentially from 11 to 14 carbon atoms.

Preferentially, the saturated fatty acid composition (C1) comprises, with respect to the total weight of the saturated fatty acid composition (C1), at least 50% by weight, preferentially at least 75% by weight, more preferentially at least 90% by weight, advantageously at least 95% by weight, or even at least 98% by weight of saturated fatty monoacid(s) with 10 to 20 carbon atoms, preferentially from 10 to 16 carbon atoms, preferentially from 11 to 14 carbon atoms.

Preferentially, the saturated fatty acid composition (C1) comprises, with respect to the total weight of the saturated fatty acid composition (C1), at least 50% by weight, preferentially at least 75% by weight, more preferentially at least 90% by weight, advantageously at least 95% by weight, or even at least 98% by weight of the same saturated fatty monoacid with 10 to 20 carbon atoms, preferentially from 10 to 16 carbon atoms, preferentially from 11 to 14 carbon atoms.

According to one embodiment, the saturated fatty acid composition (C1) comprises at least one saturated fatty acid corresponding to formula (2), preferentially at least 50% by weight, preferentially at least 75% by weight, of the same saturated fatty acid corresponding to formula (2), with respect to the total weight of the saturated fatty acid composition (C1).

[Chem 2]

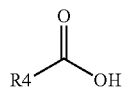

wherein R4 represents an either linear or branched monovalent alkyl radical with 9 to 19 carbon atoms, preferentially an either linear or branched alkyl with 9 to 15 carbon atoms, advantageously a linear alkyl with 10 to 13 carbon atoms.

According to one embodiment, the saturated fatty acid composition (C1) comprises at least one acid chosen from decanoic acid, undecanoic acid, lauric acid and the mixture thereof, preferentially from undecanoic acid, lauric acid and the mixture thereof.

Preferentially, the saturated fatty acid composition (C1) used in the invention comprises, with respect to the total weight of the saturated fatty acid composition (C1), at least 85% by weight of saturated fatty acids with 11 to 14 carbon atoms, preferentially at least 90% by weight of saturated fatty acids with 11 to 14 carbon atoms, more preferentially at least 95% by weight of saturated fatty acids with 11 to 14 carbon atoms, with respect to the total weight of the saturated fatty acid composition (C1).

Preferentially, the saturated fatty acid composition (C1) used in the invention comprises, with respect to the total weight of the saturated fatty acid composition (C1), at least 85% by weight of the same saturated fatty acid with 11 to 14 carbon atoms, preferentially at least 90% by weight of the same saturated fatty acid with 11 to 14 carbon atoms, more preferentially at least 95% by weight of the same saturated fatty acid with 11 to 14 carbon atoms, with respect to the total weight of the saturated fatty acid composition (C1).

The saturated fatty acid composition (C1) can be commercially available.

Unsaturated Fatty Acid Composition (C2)

The estolide composition according to the invention is obtained from an unsaturated fatty acid composition comprising, with respect to the total weight of the unsaturated fatty acid composition (C2), at least 85% by weight of mono-unsaturated fatty acids with 8 to 22 carbon atoms, with respect to the total weight of the unsaturated fatty acid composition (C2).

Preferentially, the unsaturated fatty acid composition comprises, with respect to the total weight of the unsaturated fatty acid composition (C2), at least 90% by weight of mono-unsaturated fatty acids with 8 to 22 carbon atoms, with respect to the total weight of the unsaturated fatty acid composition.

Preferentially, the mono-unsaturated fatty acids of the mono-unsaturated fatty acid composition are chosen from mono-unsaturated fatty acids with 10 to 22 carbon atoms, preferentially from 14 to 22 carbon atoms, more preferentially from 16 to 18 carbon atoms.

The mono-unsaturated fatty acids of the mono-unsaturated fatty acid composition may be either linear or branched, preferentially the mono-unsaturated fatty acids of the mono-unsaturated fatty acid composition are linear acids having an unsaturation which is not located in a terminal position.

According to one embodiment, the unsaturated fatty acid composition is obtained from either a vegetable or animal oil.

Preferentially, the unsaturated fatty acid composition (C2) comprises, with respect to the total weight of the unsaturated fatty acid composition (C2), at least 85% by weight of the same mono-unsaturated fatty acid with 8 to 22 carbon atoms, preferentially at least 85% by weight of the same mono-unsaturated fatty acid with 14 to 22 carbon atoms, with respect to the total weight of the unsaturated fatty acid composition (C2). It should be noted that the same mono-unsaturated fatty acid may be in the form of a plurality of positional isomers and/or a plurality of configurational isomers.

As defined by the present invention, two compounds are said to be "different" if the two compounds do not have the same empirical formula. As an example, two cis/trans isomers or two positional isomers are not different compounds as defined by the present invention. Two positional isomers differ in the position of the carbon-carbon double bond on the hydrocarbon chain.

Typically, the unsaturated fatty acids in the unsaturated fatty acid composition are monoacids which do not comprise any function other than the acid function and the carbon-carbon double bond.

According to one embodiment, the unsaturated fatty acid composition (C2) comprises at least one unsaturated fatty acid corresponding to the formula (3):

[Chem 3]

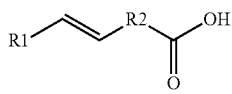

or to the formula (4):

[Chem 4]

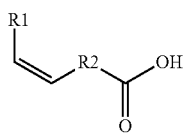

wherein:
R1 represents a hydrogen atom or an either linear or branched monovalent alkyl radical with 1 to 16 carbon atoms, preferentially from 4 to 14 carbon atoms, advantageously R1 represents a hydrogen atom or a linear alkyl with 5 to 12 carbon atoms,
R2 represents an either linear or branched divalent alkylene radical with 1 to 16 carbon atoms, preferentially an either linear or branched alkylene with 3 to 13 carbon atoms, advantageously a linear alkylene with 4 to 11 carbon atoms,
where it is understood that the sum of the carbon atoms of R1 and R2 ranges from 5 to 19.

It should be noted that the two cis/trans isomers, as illustrated e.g. by the formulas (3) and (4), can be in equilibrium in the reaction medium.

The unsaturated fatty acid composition (C2) used to obtain the estolide composition according to the invention, can comprise a mixture of at least two different unsaturated fatty acids. If the unsaturated fatty acid composition comprises a mixture of at least two different unsaturated acids, said composition preferentially comprises at least 70% by weight, more preferentially at least 80% by weight, advantageously at least 85% by weight, of the same acid and/or of the isomer thereof, with respect to the total weight of the unsaturated acid composition (C2).

According to one embodiment, the unsaturated fatty acid composition (C2) comprises oleic acid and/or the trans isomer thereof, preferentially in a proportion of at least 80% by weight, more preferentially of at least 85% by weight, or even of at least 88% by weight, with respect to the total weight of the unsaturated fatty acid composition (C2). Depending on the natural or synthetic source of the unsaturated fatty acid composition, said unsaturated compound may be in the cis form thereof and/or in the trans form thereof when used in the invention.

According to one embodiment, the unsaturated fatty acid composition (C2) used in the invention comprises, with respect to the total weight of the unsaturated fatty acid composition (C2), less than 8% by weight of poly-unsaturated acids, preferentially less than 5% by weight, even less than 3% by weight of poly-unsaturated acids.

According to a particular embodiment of the invention, the unsaturated fatty acid composition (C2) used in the invention comes from an oil rich in mono-unsaturated compounds, preferentially, the invention uses an unsaturated fatty acid composition substantially or totally free of poly-unsaturated compounds. Among the unsaturated compounds of plant origin, it is possible to choose the acids, tall oil, rapeseed oil, sunflower oil, castor oil, peanut oil, linseed oil, copra oil, olive oil, palm oil, cotton oil, corn oil, tallow oil, lard oil, palm kernel oil, soybean oil, squash seed oil, grape seed oil, argan oil, jojoba oil, sesame oil, nut oil, hazelnut oil, China wood oil, rice oil and similar oils from hybrid or genetically modified species.

Among the unsaturated compounds of animal origin, fatty acids from marine animals, fish or marine mammals and fat from terrestrial animals such as horse, beef and pork fat, can be included.

Implementation of the Addition Reaction (Step a)

The estolides according to the invention are obtained by a first step consisting of a reaction of addition of the saturated fatty acid composition (C1) to the unsaturated fatty acid composition (C2) in the presence of a catalyst in order to obtain an acid estolide composition (C3).

Such reaction is an addition reaction between the acid function of the saturated fatty acid and the carbon-carbon double bond of the unsaturated compound in acid or ester form in order to form at least one estolide.

According to one embodiment of the invention, the addition reaction (step a) is performed at a temperature ranging from 20 to 120° C., preferentially ranging from 30 to 100° C., advantageously ranging from 40 to 90° C.

Step a) can be carried out continuously or semi-continuously or in a batch.

According to one embodiment, the process of the invention involves adding the composition (C1) and the composition (C2) in a batch (simultaneous addition of all the reagents) or in a fractionated way (progressive addition of one of the two compositions (C1) or (C2) to the other composition).

According to one embodiment, the addition reaction is carried out according to one or more of the following conditions:
- the molar ratio between the unsaturated compound and the saturated fatty acid ranges from 1/10 to 1/1, preferentially from 1/8 to 1/4;
- the molar ratio between the unsaturated compound and the catalyst ranges from 1/0.1 to 1/1, preferentially from 1/0.15 to 1/0.5.

The progress of the reaction can be monitored by gas chromatography coupled to a flame ionization detector (GC-FID), according to methods known to a person skilled in the art.

The catalyst e.g. can be chosen from:
perchloric acid,
a catalyst with the formula (5) $RSO_3H$ or the sulfonate form thereof, optionally supported, where R is a hydrogen atom or a linear, branched or cyclic hydrocarbon radical with 1 to 18 carbon atoms, optionally substituted by one or more heteroatoms, e.g. nitrogen, fluorine, oxygen, sulfur, silicon,
triflates (trifluoromethylsulfonate) with the formula $CF_3SO_3^-M^+$ where M represents a chosen from bismuth, copper, aluminum and iron, and metal a catalyst in the form of a polymer with the formula (6):

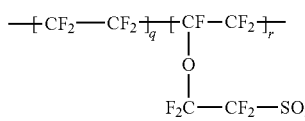
[Chem 6]

where q and r independently represent a non-zero number from 1 to 15.

The catalysts which can be used in the invention are commercially available.

The catalyst used in the invention can be either a homogeneous catalyst or a heterogeneous catalyst.

When a heterogeneous catalyst is involved, same may be a catalyst in the form of a polymer (e.g., the catalyst with the formula (6)) or the catalyst (e.g., the catalyst with the formula (5)) may be supported on a material which can be chosen from alumina, silica, etc.

According to one embodiment, the estolide composition (C3) is obtained at the end of a separation step of separating the catalyst from the estolide composition thus obtained.

According to one embodiment, the process of obtaining estolides comprises a treatment step for removing unsaturated fatty acids and/or saturated fatty acids present in the acid estolide composition (C3) and/or a separation step for separating the acid monoestolides from the acid polyestolides present in the acid estolide composition (C3), in order to obtain a treated acid estolide composition (C3bis).

The treatment step for removing unsaturated fatty acids and/or saturated fatty acids can be molecular distillation, whether or not carried out under vacuum.

The separation step for separating the acid monoestolides from the acid polyestolides can be vacuum distillation, e.g. Myers distillation or molecular distillation.

The above-mentioned separation step may be carried out either before or after the above-mentioned treatment step.

The acid estolide composition (C3) or (C3bis) can include monoestolides and/or polyestolides.

The acid estolides composition (C3) or (C3bis) typically comprises at least one estolide with the formula (7).

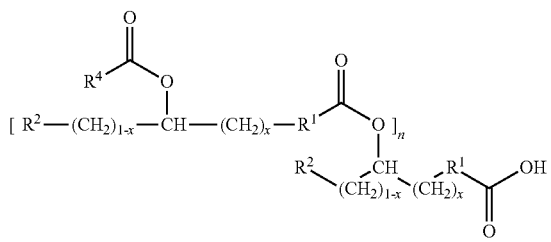
[Chem 7]

Wherein:
R1 represents a hydrogen atom or an either linear or branched monovalent alkyl radical with 1 to 16 carbon atoms, preferentially from 4 to 14 carbon atoms, advantageously R1 represents a hydrogen atom or a linear alkyl with 5 to 12 carbon atoms,
R2 represents an either linear or branched divalent alkylene radical with 1 to 16 carbon atoms, preferentially an either linear or branched alkylene with 3 to 13 carbon atoms, advantageously a linear alkylene with 4 to 11 carbon atoms, where it is understood that the sum of the carbon atoms of R1 and R2 ranges from 5 to 19,
x is equal to 0 or 1,
n is an integer greater than or equal to zero.

In one embodiment, the estolide composition (C3bis) is obtained after the separation of the monoestolides from the polyestolides. In this embodiment, the estolide composition (C3bis) typically comprises at least 60% by weight of monoestolides with the formula (8):

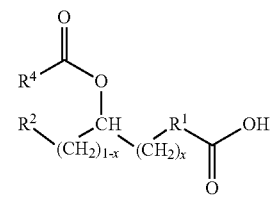
[Chem 8]

Wherein:
R1 represents a hydrogen atom or an either linear or branched monovalent alkyl radical with 1 to 16 carbon atoms, preferentially from 4 to 14 carbon atoms, advantageously R1 represents a hydrogen atom or a linear alkyl with 5 to 12 carbon atoms,
R2 represents an either linear or branched divalent alkylene radical with 1 to 16 carbon atoms, preferentially an either linear or branched alkylene with 3 to 13 carbon atoms, advantageously a linear alkylene with 4 to 11 carbon atoms,
where it is understood that the sum of the carbon atoms of R1 and R2 ranges from 5 to 19,
x is equal to 0 or 1.

The compound with the formula (8) corresponds to the compound with the formula (7) where n is equal to zero.

Alcohol Composition (C4)

The estolide composition according to the invention is an estolide ester-form composition obtained by the esterification of the acid estolide composition (C3) or, if any, of the treated acid estolide composition (C3bis) with an alcohol composition (C4).

The alcohol composition (C4) comprises at least one alcohol with 2 to 6 carbon atoms.

Preferentially, the composition (C4) comprises at least one either linear or branched, preferentially branched, aliphatic mono-alcohol with 2 to 6 carbon atoms, preferentially from 3 to 6 carbon atoms, or even from 4 to 5 carbon atoms.

Preferentially, the esterification is carried out using an alcohol composition (C4) comprising at least 85% by weight, preferentially at least 90% by weight, or even at least 95% by weight of alcohols with 2 to 6 carbon atoms, with respect to the total weight of the alcohol composition.

Preferentially, the esterification is carried out using an alcohol composition (C4) comprising at least 85% by weight, preferentially at least 90% by weight, or even at least 95% by weight of the same alcohol with 2 to 6 carbon atoms, with respect to the total weight of the alcohol composition.

Preferentially, the esterification is carried out using an alcohol composition (C4) comprising at least 85% by weight, preferentially at least 90% by weight, or even at least 95% by weight of the same alcohol with 4 to 5 carbon atoms, with respect to the total weight of the alcohol composition.

The alcohols of the alcohol composition (C4) are preferentially of biological origin.

Esterification Reaction (Step c))

Thus, the estolide ester composition (C5) is obtained after an esterification reaction of the acid estolide composition (C3) or, if any, (C3bis).

The esterification step can be carried out according to any method well known to a person skilled in the art. The esterification reaction may be carried out using the same catalyst as the catalyst used for the addition reaction (step a)) or it can be different. Preferentially, it would be the same catalyst.

The catalyst can thus have one or a plurality of the features described above in the context of the addition reaction.

The estolide ester composition (C5) typically comprises at least one estolide ester with the formula (1):

[Chem. 1]

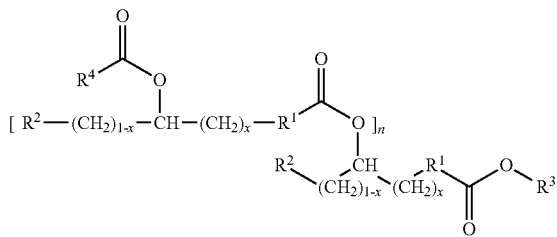

wherein:
R1 is an either linear or branched alkylene radical with 1 to 16 carbon atoms,
R2 is a hydrogen atom or an either linear or branched alkyl radical with 1 to 16 carbon atoms,
R3 is an either linear or branched alkyl radical with 2 to 6 carbon atoms,
R4 is an either linear or branched alkyl radical with 7 to 19 carbon atoms,
x is an integer equal to 0 or 1,
where it is understood that the sum of the carbon atoms of the radicals R1 and R2 ranges from 5 to 19,
n is an integer greater than or equal to zero.

The estolide ester composition (C5) can undergo a separation step for separating monoestolides from polyestolides, particularly where such separation did not take place before the esterification step.

According to one embodiment, the process of obtaining estolides comprises a treatment step for removing the unsaturated fatty acid esters and/or the saturated fatty acid esters present in the estolide ester composition (C5) and/or a separation step for separating the ester monoestolides from the ester polyestolides present in the acid ester composition (C5), in order to obtain a treated estolide ester composition (C5bis).

The treatment step for removing unsaturated fatty acid esters and/or saturated fatty acid esters can be molecular distillation, whether or not carried out under vacuum.

The separation step for separating the monoestolide esters from the polyestolide esters may be vacuum distillation, e.g. a Myers or molecular distillation type distillation.

The above-mentioned separation step may be carried out either before or after the above-mentioned treatment step.

According to such embodiment, the treated estolide ester composition (C5bis) preferably comprises at least 60% by weight of monoestolides corresponding to the formula (9):

[Chem. 9]

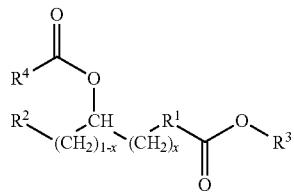

wherein:
R1 is an either linear or branched alkylene radical having from 1 to 16 carbon atoms,
R2 is a hydrogen atom or an either linear or branched alkyl radical having from 1 to 16 carbon atoms,
R3 is an either linear or branched alkyl radical having 2 to 6 carbon atoms,
R4 is an either linear or branched alkyl radical with 7 to 19 carbon atoms,
x is an integer equal to 0 or 1,
where it is understood that the sum of the carbon atoms of the radicals R1 and R2 ranges from 5 to 19.

The compound with the formula (9) corresponds to the compound with the formula (1) where n is equal to zero.

Preferentially, in the compound with the formula (9):
R1 represents a hydrogen atom or an either linear or branched monovalent alkyl radical with 4 to 14 carbon atoms, advantageously R1 represents a hydrogen atom or a linear alkyl with 5 to 12 carbon atoms, and
R2 represents an either linear or branched divalent alkylene radical with 3 to 13 carbon atoms, advantageously a linear alkylene with 4 to 11 carbon atoms, where it is understood that the sum of the carbon atoms of R1 and R2 ranges from 8 to 19, advantageously from 12 to 19.

Preferentially, the estolide ester composition is obtained by a process that does not include a subsequent step of hydrogenating the estolide ester composition (C5) or, if any (C5bis).

The estolide ester composition (C5) or treated estolide esters (C5bis) will refer to the composition resulting from the process, after the separation of the catalyst.

The progress of the process, and in particular of the addition reaction, can be monitored by gas chromatography coupled to a flame ionization detector (GC-FID), according to methods known to a person skilled in the art.

As defined in the present invention, conversion refers to the amount in percentage by weight of unsaturated compound(s) which have reacted, and selectivity refers to the amount in percentage by weight of monoestolides formed with respect to the total weight of the products formed (the selectivity calculation thus does not take into account the reactants nor the catalyst).

According to a particular embodiment, the unsaturated acid composition (C2) comprises at least 85% by weight of oleic acids and the saturated fatty acid composition (C1) comprises at least 70% by weight of linear fatty acids with 10 to 14 carbon atoms, and the alcohol composition (C4) comprises at least 70% by weight of branched alcohols with 4 to 6 carbon atoms.

According to such embodiment, the estolide ester composition (C5) comprises at least 70% by weight of estolide(s) with the formula (10):

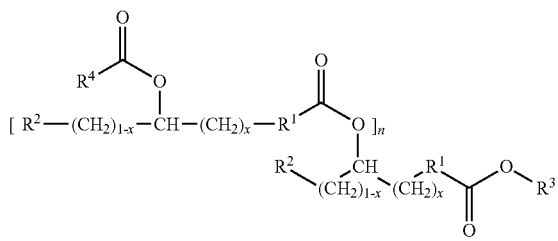

wherein:
R1 is a linear alkylene radical with 1 to 14 carbon atoms,
R2 is a hydrogen atom or an either linear or branched alkyl radical with 1 to 14 carbon atoms,
R3 is a branched alkyl radical with 4 to 6 carbon atoms,
R4 is a linear alkyl radical with 9 to 13 carbon atoms,
x is an integer equal to 0 or 1,
where it is understood that the sum of the carbon atoms of the radicals R1 and R2 is equal to 15,
n is an integer greater than or equal to zero.

Preferentially, the estolide composition (C5) or, if any (C5bis) has an iodine value of less than or equal to 12 g/100 g of iodine, preferentially less than or equal to 10 g/100 g of iodine, more preferentially ranging from 1 to 10 g/100 g of iodine, as measured according to the NF EN ISO 3961 method. The manufacturing process according to the invention can be used for obtaining low iodine values, and hence not needing a subsequent hydrogenation step.

Preferentially, the estolide composition (C5) has an estolide number ranging from 1.0 to 1.3, preferentially from 1.0 to 1.2. It should be noted that even in the absence of the separation of the monoestolides from the polyestolides, the estolide ester composition (C5) will preferentially have an estolide number ranging from 1.0 to 1.3, or even from 1.0 to 1.2.

When the process for preparing the estolide ester composition involves a step of separating the monoestolides from the polyestolides, then the estolide ester composition thus treated will have an estolide number ranging from 1.0 to 1.1, preferentially of about 1.0.

The estolide number can be determined by NMR analysis.

The estolide ester composition (C5) or if any (C5bis) according to the invention, advantageously has a biodegradability at 28 days of at least 60%, preferentially at least 70%, more preferentially at least 75% and advantageously at least 80%, as measured according to the OECD 306 method.

The estolide ester composition (C5) or if any (C5bis) according to the invention advantageously comprises a concentration of carbon of biological (non-petrochemical) origin, also called biocarbon concentration, of at least 90% by weight with respect to the total weight of carbon. The biocarbon concentration can be measured according to the standard ASTM D6866.

A material of renewable origin or biomaterial is an organic material wherein the carbon comes from $CO_2$ recently fixed (on a human timescale) by photosynthesis from the atmosphere. A biomaterial (carbon of 100% natural origin) has an isotopic ratio of $^{14}C/^{12}C$ greater than $10^{-12}$, typically about $1.2\times10^{-12}$, whereas a fossil material (petrochemical) has a ratio equal to zero. In fact, the isotopic $^{14}C$ is formed in the atmosphere and then integrated by photosynthesis, according to a time scale of a few tens of years at most. The half-life of $^{14}C$ is 5,730 years. Thus, the materials coming from photosynthesis, namely plants in general, necessarily have a maximum concentration of isotope $^{14}C$.

Determining the concentration of biomaterial or bio-carbon is given as per the standards ASTM D 6866-12, method B (ASTM D 6866-06) and ASTM D 7026 (ASTM D 7026-04).

Uses

The estolide composition according to the invention can be used as a cosmetic, dermatological or pharmaceutical composition for topical application.

The estolide composition according to the invention provides a non-irritating, low-odor and biodegradable composition.

The estolide composition according to the invention can be used for obtaining stable topical compositions.

Moreover, the estolide composition according to the invention is emollient due to a soft and nourishing finish (touch).

The estolide composition according to the invention can be used to replace silicone-type ingredients such as dimethicone or polyisobutenes, in topical compositions.

In addition to the improved physico-chemical and sensory properties thereof due to the intrinsic composition of the estolide composition, the estolide composition according to the invention has good miscibility with the other fatty substances conventionally used in the cosmetic, dermatological or pharmaceutical fields.

In particular, the estolide composition according to the invention exhibits good miscibility with the fatty substances chosen from the group comprising: hydrocarbon oils of biological or petrochemical origin, vegetable oils, vegetable butters, fatty ethers and alcohols, oily esters (other than estolides), alkanes and silicone oils.

The subject matter of the invention is also the cosmetic, dermatological or pharmaceutical use of the estolide composition according to the invention for topical application.

The further subject matter of the invention is the cosmetic, dermatological or pharmaceutical use of the estolide composition according to the invention as a skin care product (serums, creams, balms, etc.), as a hygiene product, as a suncare/after-sun product, as a make-up-removing product, as a perfumed product, as an antiperspirant product.

The further subject matter of the invention is a cosmetic, dermatological or pharmaceutical method for skin treatment, comprising at least one step of applying an estolide composition according to the invention on the skin, the nails, the lips, the scalp or the hair.

Finally, the invention further covers a cosmetic treatment process comprising at least one step of applying, preferentially by spreading, the estolide composition according to the invention on the skin, the nails, the lips, the scalp or the hair.

Cosmetic, Dermatological and Pharmaceutical Compositions

A further subject matter of the invention is a topical composition comprising the estolide composition according to the invention and at least one additive and/or at least one fatty substance, said additive and said fatty substance being distinct from each other and distinct from the ingredients of the estolide composition.

The fatty substance can be chosen from hydrocarbon oils of biological or petrochemical origin, vegetable oils, vegetable butters, ethers and fatty alcohols, oily esters (different from estolides), alkanes and silicone oils.

Hydrocarbon oils are fatty substances coming from petrochemical processes. As an example, mineral oils, isoparaffins, waxes, paraffins, polyisobutenes or polydecenes can be cited.

Examples of vegetable oils include in particular wheat germ oil, sunflower oil, grape seed oil, sesame oil, corn oil, apricot, castor oil, shea oil, avocado oil, olive oil, soybean oil, sweet almond oil, palm oil, rapeseed oil, cotton oil, hazelnut oil, macadamia oil, jojoba oil, alfalfa oil, *papaver* seed oil, pumpkin seed oil, sesame oil, squash oil, rapeseed oil, blackcurrant oil, evening primrose oil, millet oil, barley oil, *quinoa* oil, rye oil, safflower oil, candlenut oil, passion flower oil, musk rose oil or *camellia* oil. Vegetable butters are fatty substances which have the same properties as vegetable oils. The difference between the two consists in the fact that the butters are in solid form at room temperature. Furthermore, unlike vegetable oils, the raw material from which a butter is extracted (pulp, seeds or almonds) is heated after being ground for the extraction of the fat. Like vegetable oils, butters can be refined to ensure better preservation, neutralize odors, improve color and consistency. Rich in antioxidants and nourishing, the cosmetic properties of vegetable butters improve the elasticity of the skin, protect against external aggressions by leaving a protective film on the epidermis and thus reducing dehydration, repair and soothe by regenerating the natural hydrolipidic film of the skin. Examples of vegetable butters include in particular shea butter, cocoa butter, mango butter, shorea butter and olive butter.

Ethers and fatty alcohols are long-chain, fatty, waxy substances with remarkable properties, in particular film-forming, emollient, moisturizing, softening and protective properties. Same act as moisturizing oils and emulsifiers. Examples of fatty alcohol or ethers are: cetyl alcohol, stearyl alcohol, myristyl alcohol, auryl alcohol, behenyl alcohol, cetearyl alcohol, dicaprylyl ethers, stearyl ethers or octyldodecanol (identified by the INCI name thereof).

The oily esters or esterified oils (distinct of the estolides of the invention) are the product of a reaction between fatty acids (acids with longer chains, such as e.g. stearic acid, oleic acid, palmitic acid) and alcohols (fatty alcohols or polyols such as glycerol). Such oils may contain substances coming from petrochemistry, as is the case for isopropyl palmitate. Examples of oily esters are caprylic capric triglyceride, coco caprylate caprate, oleyl erucate, oleyl linoleate, decyl oleate or PPG-3 benzyl ether myristate (identified by the INCI name thereof).

Silicone or polysiloxane oils are understood to mean oils comprising at least one silicon atom, and in particular at least one Si—O group. As silicone oil, phenylpropyldimethylsiloxysilicate, dimethicones or cyclopentasiloxane (identified by the INCI name thereof) can be cited in particular.

The additive, distinct from the fatty substance and from the estolide composition, can be chosen from any adjuvant or additive usually used in the fields considered and in particular in the cosmetic, dermatological or pharmaceutical fields. Of course, a person skilled in the art will take care to select the possible additive(s) of the composition according to the invention such that the advantageous properties intrinsically associated with the emollient composition in accordance with the invention are not, or are not substantially, altered by the intended addition. Among the conventional adjuvants which may be contained (depending on the water-soluble or fat-soluble nature of the adjuvants), mention can be made in particular of anionic foaming surfactants (such as sodium lauryl ether sulfate, sodium alkyl phosphate, sodium trideceth sulfate), amphoteric foaming surfactants (such as alkyl betaine, disodium coamphodiacetate) or nonionic foaming surfactants with an HLB greater than 10 (such as POE/PPG/POE, alkylpolyglucoside, polyglyceryl-3-hydroxylauryl ether); preservatives; sequestering agents (EDTA); antioxidants; fragrances; coloring materials such as soluble dyes, pigments and nacres; matting, tensors, whitening or exfoliating fillers; cosmetic active ingredients with the effect of improving the cosmetic properties of the skin, either hydrophilic or lipophilic; electrolytes; hydrophilic or lipophilic, anionic, nonionic, cationic or amphoteric, thickening, gelling or dispersing polymers; slimming agents such as caffeine; optical brighteners; antisebohrreics; water-soluble or fat-soluble vitamins such as vitamin A (retinol), vitamin E (tocopherol), vitamin C (ascorbic acid), vitamin B5 (panthenol), vitamin B3 (niacinamide), derivatives of said vitamins (especially esters); and the mixture thereof. The amounts of such various cosmetic adjuvants are those conventionally used in the field considered, and e.g. the cosmetic composition comprises an overall concentration ranging from 0.01 to 20% by weight of additives with respect to the total weight of the composition. Whenever the cosmetic, dermatological or pharmaceutical composition of the invention is a dermatological or pharmaceutical composition, said composition may comprise one or more therapeutic active principles. As active agents which can be used in the dermatological or pharmaceutical composition of the invention, mention can be made, e.g., of sunscreens; antiseptics; antibacterial active agents such as 2,4,4'-trichloro-2'-hydroxydiphenyl ether (or triclosan), 3,4,4'-trichlorocarbanilide (or triclocarban); antimicrobials such as benzoyl peroxide or niacin (vit. PP); and mixtures thereof.

Such cosmetic, dermatological or pharmaceutical composition comprises a physiologically acceptable medium, i.e. which does not have harmful side effects and in particular which does not produce redness, heating, tightness or tingling which are unacceptable to a user.

According to one embodiment, the cosmetic, dermatological or pharmaceutical composition has a concentration of estolide composition according to the invention ranging from 0.5 to 80%, preferentially from 1 to 50% and advantageously from 5 to 30% by weight with respect to the total weight of the cosmetic, dermatological or pharmaceutical composition.

According to one embodiment of the invention, the cosmetic, dermatological or pharmaceutical composition comprises, with respect to the total weight of the cosmetic, dermatological or pharmaceutical composition:
 from 0.5 to 80% by weight, preferentially from 1 to 50% by weight and advantageously from 5 to 30% by weight, of the estolide composition according to the invention,
 from 0 to 90% by weight, preferentially from 5 to 80% by weight and advantageously from 10 to 70% by weight, preferentially from 20 to 60% by weight and advantageously from 30 to 50% by weight, of fatty substances,
 0 to 20% by weight of additives,
 0 to 20% by weight of therapeutic active ingredients,
 where it is understood that the composition comprises at least one additive or at least one fatty substance.

According to one embodiment of the invention, the cosmetic, dermatological or pharmaceutical composition comprises, with respect to the total weight of the cosmetic, dermatological or pharmaceutical composition:
 from 0.5 to 80% by weight, preferentially from 1 to 50% by weight and advantageously from 5 to 30% by weight, of the estolide composition according to the invention,
 from 0 to 90% by weight, preferentially from 5 to 80% by weight and advantageously from 10 to 70% by weight, preferentially from 20 to 60% by weight and advantageously from 30 to 50% by weight, of fatty substances chosen from hydrocarbon oils of biological or petrochemical origin, vegetable oils, vegetable butters, fatty ethers and alcohols, oily esters (different from estolides), alkanes and silicone oils, 0 to 20% by weight of additives chosen from anionic, amphoteric or nonionic foaming surfactants with HLB greater than 10; preservatives; sequestering agents; antioxidants; perfumes; coloring materials; mattifying, tensing, whitening or exfoliating fillers; cosmetic active agents with the effect of improving the cosmetic properties of the skin, either hydrophilic or lipophilic; electrolytes; hydrophilic or lipophilic, anionic, nonionic, cationic or amphoteric, thickening, gelling or dispersing polymers; slimming agents; optical brighteners; antisebohrreics; and mixtures thereof, optionally, from 0 to 20% by weight of therapeutic active ingredients, where it is understood that the composition comprises at least one additive or at least one fatty substance.

The cosmetic, dermatological or pharmaceutical composition according to the invention can thus be an anhydrous composition, an emulsion such as a water-in-oil (W/O) emulsion, an oil-in-water (O/W) emulsion or a multiple emulsion (in particular W/O/W or O/W/O), a nano-emulsion, or further a dispersion.

The cosmetic, dermatological or pharmaceutical composition according to the invention is in the form of a variably flexible cream or of a sprayable emulsion. Same could be e.g. a composition for removing make-up or cleansing the skin, the lips, an after-sun composition, a composition for massaging the skin, a shower balm composition, an antiperspirant composition, a mask composition, a restorative balm composition, a scrub and/or exfoliating composition for both the face and the hands (when same contains exfoliating particles), a make-up composition, a shaving composition, an after-shave balm composition, a perfumed composition, a composition for wipes or further a sprayable composition. The cosmetic, dermatological or pharmaceutical composition according to the invention can further be a sunscreen composition when same includes at least one sunscreen.

The cosmetic, dermatological or pharmaceutical composition according to the invention is a cosmetic composition when same provides only a cosmetic effect. Typically, the cosmetic composition according to the invention is free of therapeutic active agents.

On the contrary, the cosmetic, dermatological or pharmaceutical composition according to the invention is a dermatological or pharmaceutical composition when same provides a therapeutic effect. Typically, the dermatological or pharmaceutical composition according to the invention comprises at least one therapeutic active agent, e.g. chosen from sunscreens; water-soluble or fat-soluble vitamins such as vitamin A (retinol), vitamin E (tocopherol), vitamin C (ascorbic acid), vitamin B5 (panthenol), vitamin B3 (niacinamide), derivatives of said vitamins (especially esters) and the mixtures thereof; antiseptics; antibacterial active agents such as 2,4,4'-trichloro-2'-hydroxydiphenyl ether (or triclosan), 3,4,4'-trichlorocarbanilide (or triclocarban); antimicrobials such as benzoyl peroxide, niacin (vit. PP); and the mixtures thereof.

Uses of the Cosmetic, Dermatological or Pharmaceutical Composition

A further subject matter of the invention is the cosmetic, dermatological or pharmaceutical use of the composition as defined above for topical application, e.g. on the skin, the nails, the lips, the scalp or the hair.

A further subject matter of the invention is the cosmetic, dermatological or pharmaceutical use of the composition as defined above as a skin care product (serums, creams, balms, etc.) as a hygiene product, as a suncare/after-sun product, as a make-up product, as a make-up remover product, as a perfumed product, as an antiperspirant product.

Another further subject matter of the invention is a cosmetic, dermatological or pharmaceutical process for treating the skin, the nails, the lips, the scalp or the hair, comprising at least one step of applying a dermatological or pharmaceutical as defined above, on the skin, the nails, the lips, the scalp or the hair.

The composition of the invention can further be used for the formulation of cosmetic compositions, dermatological compositions or pharmaceutical compositions comprising other components or other phases than same described above. This can relate in particular to the formulation of care, hygiene or make-up compositions.

EXAMPLES

Hereinafter in the present description, examples are given as an illustration of the present invention and are in no way intended to limit the scope thereof.

Example 1: Preparation of Estolide Compositions

The example describes the estolide compositions which were prepared.

The following saturated fatty acid compositions were used:

AGSat1=more than 95% by weight of lauric acid, with respect to the total weight of AGSat1;

AGSat2=more than 95% by weight of heptanoic acid, with respect to the total weight of AGSat2;

AGSat3=more than 95% by weight of nonanoic acid, with respect to the total weight of AGSat3.

The following unsaturated fatty acid compositions were used:

AGinsat1=at least 90% by weight of oleic acids and less than 3% by weight of poly-unsaturated compounds, with respect to the total weight of AGinsat1;

AGinsat2=88% by weight of oleic acids and 3 to 8% by weight of poly-unsaturated compounds, with respect to the total weight of AGinsat2;

AGinsat3=83% by weight of oleic acids and 3 to 10% by weight of poly-unsaturated compounds, with respect to the total weight of AGinsat3.

The following alcohol compositions were used:
OH1=more than 95% by weight of 3-methyl butanol, with respect to the total weight of OH1;
OH2=more than 95% by weight of 2-octanol, with respect to the total weight of OH2;
OH3=more than 95% by weight of 2-ethylhexanol, with respect to the total weight of OH3.

The estolide ester compositions are prepared according to two processes, one using a separation of the monoestolides from the polyestolides and the other not using such a separation.

The catalyst used is perchloric acid.

The preparation process comprises the following steps:
(A) an addition reaction of the saturated fatty acid composition to the unsaturated fatty acid composition in the presence of the catalyst at a temperature of 60° C. in order to obtain an acid ester composition, and (b) optionally, a vacuum distillation separation step for separating acid monoestolides from acid polyestolides in order to obtain a treated acid estolide composition, and (c) an esterification reaction of the acid estolides of the acid estolide composition (C3) using the alcohol composition (C4) at a temperature of 30° C. in order to obtain an estolide ester composition.

Table 2 below shows all the compositions of estolides which were prepared.

TABLE 2

| | Saturated fatty acids | Unsaturated fatty acids | alcohols | Separation (step b) | Iodine number (g/100 g 12) | Number of estolides |
|---|---|---|---|---|---|---|
| CC1 | AGSat2 | AGinsat1 | OH1 | Yes | Not measured | 1.0 |
| CC2 | AGSat3 | AGinsat1 | OH1 | Yes | 1.9 | 1.0 |
| CC3 | AGSat1 | AGinsat3 | OH1 | Yes | 4.5 | 1.0 |
| CC4 | AGSat1 | AGinsat1 | OH2 | Yes | 2.6 | 1.0 |
| CC5 | AGSat1 | AGinsat1 | OH3 | Yes | 2.6 | 1.0 |
| CI1 | AGSat1 | AGinsat1 | OH1 | Yes | 2.6 | 1.0 |
| CI2 | AGSat1 | AGinsat1 | OH1 | No | 5.9 | 1.1 |
| CI3 | AGSat1 | AGinsat2 | OH1 | Yes | 2.5 | 1.0 |

Example 2: Evaluation of the Sensory Properties of Estolide Compositions

The estolide ester compositions prepared in example 1 were tested and evaluated in terms of sensory properties.

The products were evaluated from a sensory point of view by a panel of 5 members. Of these 5 members, three held degrees in esthetics.

The criteria to be evaluated were strictly defined and presented to the panelists prior to the investigation. The criteria were defined as follows:

Penetration: when the product was applied, same disappeared quickly. Did not leave any residue on the skin.

Brightness of the skin: Bright=once the product was applied, the skin was brighter.

Odor: after application, the assessment of odor was performed on the area where applied.

Irritation: After application, assessment of irritation was performed on the area where the product was applied.

Creamy: when the product was not smooth, sticky upon application, said was called raspy (the opposite of soft)

Greasy residue: after applying of the product, the product left a greasy residue on the skin The sensory and organoleptic analysis by the panel was performed on the underside of the forearm by depositing with a spatula, the same amount of each composition to be tested, and the product was then applied using the fingers. The amount of product applied was reproducible for the same tester.

All sensory analysis took place blind in an isolated room: a person which was not part of the panel, prepared the samples of products to be tested in 5 ml plastic jars, labeled 1 to 5. No name appeared on the labels, only the number will be a marker for the panel.

The results are shown in Table 3:
penetration on the skin: if the product penetrated well, the result is OK and if the product did not penetrate well, the result is Not-OK;
brightness: if the product was bright, the result is OK and if the product was not bright, the result is Not-OK;
odor: if the product did not have a strong odor, the result is OK and if the product had a strong odor, the result is Not-OK;
irritation: if the product was not irritating, the result is OK and if the product was irritating, the result is Not-OK;
raspy: If the product was not smooth, the result is OK and if the product was not smooth, the result is Not-OK;
sensation of grease on the skin: if the product did not leave a greasy sensation, the result is OK and if the product leaves a sensation of fat, the result is Not-OK.

TABLE 3

| | penetration | brightness | odor | irritation | raspy | Greasy sensation |
|---|---|---|---|---|---|---|
| CC1 | Not-OK | | Not-OK | | Not-OK | |
| CC2 | Not-OK | | Not-OK | Not-OK | | |
| CC3 | OK | OK | OK | OK | Not-OK | Not-OK |
| CC4 | Not-OK | OK | OK | OK | Not-OK | Not-OK |
| CC5 | Not-OK | OK | OK | OK | OK | Not-OK |
| CI1 | OK | OK | OK | OK | OK | OK |
| CI2 | OK | OK | OK | OK | OK | OK |
| CI3 | OK | OK | OK | OK | OK | OK |

The results of Table 3 show that the estolide compositions according to the invention have better sensory properties than the comparative estolide compositions.

We claim:

1. An estolide ester composition obtained by the process comprising:
   a) an addition reaction of a saturated fatty acid composition (C1) to an unsaturated fatty acid composition (C2) in the presence of a catalyst in order to obtain an acid estolide composition (C3), and
   b) optionally, a treatment step for removing unsaturated fatty acids and/or saturated fatty acids from the acid estolide composition (C3) and/or a separation step for separating the acid monoestolides from the acid polyestolides present in the acid estolide composition (C3) in order to obtain a treated acid estolide composition (C3bis), and
   c) an esterification reaction of the acid estolides of the acid estolide composition (C3), or, if any, of the treated acid estolide composition (C3bis), using an alcohol composition (C4) comprising one or more linear or branched alcohols with 2 to 6 carbon atoms, in order to obtain an estolide ester composition (C5),
   said saturated fatty acid composition (C1) comprising saturated fatty acids with 10 to 20 carbon atoms,
   said unsaturated fatty acid composition (C2) comprising at least 85% by weight of mono-unsaturated fatty acids with 8 to 22 carbon atoms, with respect to the total weight of the unsaturated fatty acid composition (C2).

2. The estolide ester composition according to claim 1, wherein the acid estolide composition (C3) undergoes a treatment step to remove unsaturated fatty acids and/or saturated fatty acids, in order to obtain a treated acid estolide composition (C3bis).

3. The estolide ester composition according to claim 1, wherein the acid estolide composition (C3) or if any (C3bis) undergoes a separation step for separating the acid monoestolides from the acid polyestolides present in the acid estolide composition.

4. The estolide ester composition according to claim 1, wherein, at the end of the esterification reaction, the estolide ester composition (C5) undergoes a treatment step for removing the alcohols.

5. The estolide ester composition according to claim 1, wherein it comprises at least compounds with the formula (I):

[Chem. 1]

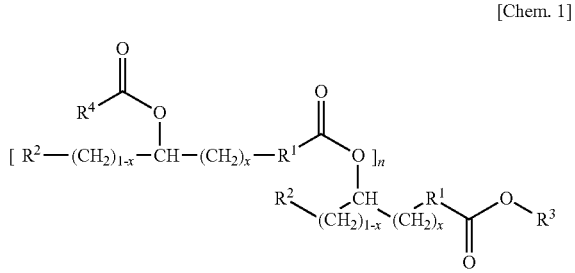

wherein:
R1 is a linear or branched alkylene radical with 1 to 19 carbon atoms,
R2 is a hydrogen atom or a linear or branched alkyl radical with 1 to 19 carbon atoms,
R3 is a linear or branched alkyl radical with 2 to 6 carbon atoms,
R4 is a linear or branched alkyl radical with 9 to 19 carbon atoms,
x is an integer equal to 0 or 1,
where it is understood that the sum of the carbon atoms of the radicals R1 and R2 ranges from 5 to 19,
n is an integer greater than or equal to zero.

6. The estolide ester composition according to claim 5, wherein it contains at least 30% by weight of compounds with the formula (I), with respect to the total weight of the estolide ester composition.

7. The estolide ester composition according to claim 1, wherein it has an iodine number lower than or equal to 12 g/100 g of iodine as measured according to the NF EN ISO 3961 method.

8. The estolide ester composition according to any claim 1, having an estolide number of from 1.0 to 1.3.

9. Method for preparing a cosmetic composition, the method comprising using the estolide ester composition according to claim 1.

10. A cosmetic composition comprising:
at least one estolide ester composition according to claim 1, and
at least one fatty substance and/or at least one cosmetic additive, said fatty substance and said cosmetic additive being different from said estolide esters.

11. The cosmetic composition according to claim 10, comprising, with respect to the total weight of the cosmetic composition:
from 1 to 80% by weight of estolide ester composition(s),
from 1 to 80% by weight of fatty substances other than the estolides chosen from hydrocarbon oils, vegetable oils, vegetable butters, fatty ethers and alcohols, oily esters, alkanes and silicone oils,
from 0.1 to 30% by weight of cosmetic additives chosen from surfactants, preservatives, sequestering agents, antioxidants, fragrances, coloring materials, fillers, thickeners, slimming agents, and mixtures thereof.

12. The composition according to claim 1, wherein the acid estolide composition (C3) undergoes a treatment step by molecular distillation to remove unsaturated fatty acids and/or saturated fatty acids, in order to obtain a treated acid estolide composition (C3bis).

13. The composition according to claim 1, wherein, at the end of the esterification reaction, the estolide ester composition (C5) undergoes a treatment step by molecular distillation for removing the alcohols.

14. The composition according to claim 5, wherein it contains at least 40% by weight of compounds with the formula (I), with respect to the total weight of the estolide ester composition.

15. The composition according to claim 1, wherein it has an iodine number from 1 to 10 g/100 g of iodine, as measured according to the NF EN ISO 3961 method.

16. Method according to claim 9, wherein the estolide composition is used as an emollient of the cosmetic composition.

17. The cosmetic composition according to claim 10, comprising, with respect to the total weight of the cosmetic composition:
i. from 5 to 50% by weight of estolide ester composition (s),
ii. from 20 to 60% by weight of fatty substances other than the estolides chosen from hydrocarbon oils, vegetable oils, vegetable butters, fatty ethers and alcohols, oily esters, alkanes and silicone oils,
iii. from 1 to 20% by weight of cosmetic additives chosen from surfactants, preservatives, sequestering agents, antioxidants, fragrances, coloring materials, fillers, thickeners, slimming agents, and mixtures thereof.

18. An estolide ester composition obtained by the process comprising:
a) an addition reaction of a saturated fatty acid composition (C1) to an unsaturated fatty acid composition (C2) in the presence of a catalyst in order to obtain an acid estolide composition (C3), and
b) optionally, a treatment step for removing unsaturated fatty acids and/or saturated fatty acids from the acid estolide composition (C3) and/or a separation step for separating the acid monoestolides from the acid polyestolides present in the acid estolide composition (C3) in order to obtain a treated acid estolide composition (C3bis), and
c) an esterification reaction of the acid estolides of the acid estolide composition (C3), or, if any, of the treated acid estolide composition (C3bis), using an alcohol composition (C4) comprising one or more linear or branched alcohols with 2 to 6 carbon atoms, in order to obtain an estolide ester composition (C5),
said saturated fatty acid composition (C1) comprising saturated fatty acids with 10 to 20 carbon atoms,
said unsaturated fatty acid composition (C2) comprising at least 85% by weight of mono-unsaturated fatty acids with 8 to 22 carbon atoms, with respect to the total weight of the unsaturated fatty acid composition (C2),
wherein the unsaturated fatty acids in the unsaturated fatty acid composition are monoacids which do not comprise any function other than the acid function and the carbon-carbon double bond.

* * * * *